United States Patent
Kreindel et al.

(10) Patent No.: US 7,241,291 B2
(45) Date of Patent: Jul. 10, 2007

(54) METHOD AND SYSTEM FOR SKIN TREATMENT USING LIGHT ENERGY AND SKIN DEFORMATION

(75) Inventors: Michael Kreindel, Haifa (IL); Simon Eckhouse, Haifa (IL)

(73) Assignee: Syneron Medical Ltd., Yokneam (IL)

( * ) Notice: Subject to any disclaimer, the term of this patent is extended or adjusted under 35 U.S.C. 154(b) by 176 days.

(21) Appl. No.: 10/858,474

(22) Filed: Jun. 2, 2004

(65) Prior Publication Data
US 2005/0273089 A1    Dec. 8, 2005

(51) Int. Cl.
*A61B 18/18*    (2006.01)
*A61N 5/06*    (2006.01)
(52) U.S. Cl. ............... 606/9; 606/3; 607/88; 607/91
(58) Field of Classification Search ............... 606/2, 606/3, 7–10; 607/88–91; 128/898
See application file for complete search history.

(56) References Cited

U.S. PATENT DOCUMENTS

| | | | |
|---|---|---|---|
| 5,405,368 A | 4/1995 | Eckhouse | |
| 5,425,754 A * | 6/1995 | Braun et al. | 607/88 |
| 5,669,916 A | 9/1997 | Anderson | |
| 5,720,772 A * | 2/1998 | Eckhouse | 607/88 |
| 5,735,844 A * | 4/1998 | Anderson et al. | 606/9 |
| 5,961,543 A * | 10/1999 | Waldmann | 607/88 |
| 6,214,034 B1 * | 4/2001 | Azar | 607/89 |
| 6,228,074 B1 * | 5/2001 | Almeida | 606/9 |
| 6,235,015 B1 * | 5/2001 | Mead et al. | 606/9 |
| 6,702,808 B1 * | 3/2004 | Kreindel | 606/9 |

* cited by examiner

*Primary Examiner*—A. Farah
(74) *Attorney, Agent, or Firm*—Browdy and Neimark, PLLC

(57) ABSTRACT

A system and method for the treatment of a skin comprising. The system comprises an applicator having a cavity and one or more light sources configured to irradiate the cavity with optical energy simultaneously from at least two directions. The applicator is applied to the skin and a region of skin is made to protrude into the cavity. The protruding region of skin is then irradiated with optical energy from the one or more light sources simultaneously from at least two directions.

7 Claims, 2 Drawing Sheets

METHOD AND SYSTEM FOR SKIN TREATMENT USING LIGHT ENERGY AND SKIN DEFORMATION

FIELD OF THE INVENTION

The present invention relates to methods and devices for skin treatments.

BACKGROUND OF THE INVENTION

The most popular cosmetic treatments involving irradiation of the skin with optical energy are hair removal, and the removal of vascular and pigmented lesions. These treatments are based on selective light absorption by the target in comparison to the surrounding skin tissue so as to heat the target to a temperature that is sufficiently high to cause thermal destruction of the target without raising the surrounding skin to damaging levels. Two types of devices are common in these treatments: one uses laser radiation, while the other uses filtered light from a light source. U.S. Pat. No. 5,405,368 describes a device for skin treatment comprising an incoherent light source. U.S. Pat. No. 5,669,916 describes use of a laser for hair removal. The main limitation of these methods is the high absorption of optical energy by the epidermis and the attenuation of the energy with increasing penetration depth due to light absorption and scattering.

SUMMARY OF THE INVENTION

The present invention provides a method system for skin treatment using light. In accordance with the method of the invention, a region of skin is made to protrude from the skin surface that is illuminated with light from at least two directions. The parameters of the light energy are adjusted to destroy a skin target within the skin. Since the target is simultaneously irradiated from at least two different directions, the target can be heated to an ablative temperature while the temperature of the skin surface is heated to a lower temperature than it would if the same total light energy density were to be applied to the skin surface from a single direction. The protruding region should be small enough to allow the optical energy to reach the center of the protruding region and create a sufficiently high light energy density inside the protruding region of the skin. The size of protruding zone can be varied from 3 mm to 10 mm depending on the target depth.

Thus in its first aspect the invention provides a system for the treatment of a skin comprising an applicator having a cavity and comprising one or more light sources configured to irradiate the cavity with optical energy simultaneously from at least two directions.

In its second aspect, the invention provides a method for treating skin with optical energy comprising:
 (a) applying to the skin an applicator having a cavity and comprising one or more light sources configured to irradiate the cavity with optical energy simultaneously from at least two directions;
 (b) causing a region of skin to protrude into the cavity; and
 (c) irradiating the protruding region of skin with optical energy from the one or more light sources simultaneously from at least two directions.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF PREFERRED EMBODIMENTS

Figure 1:
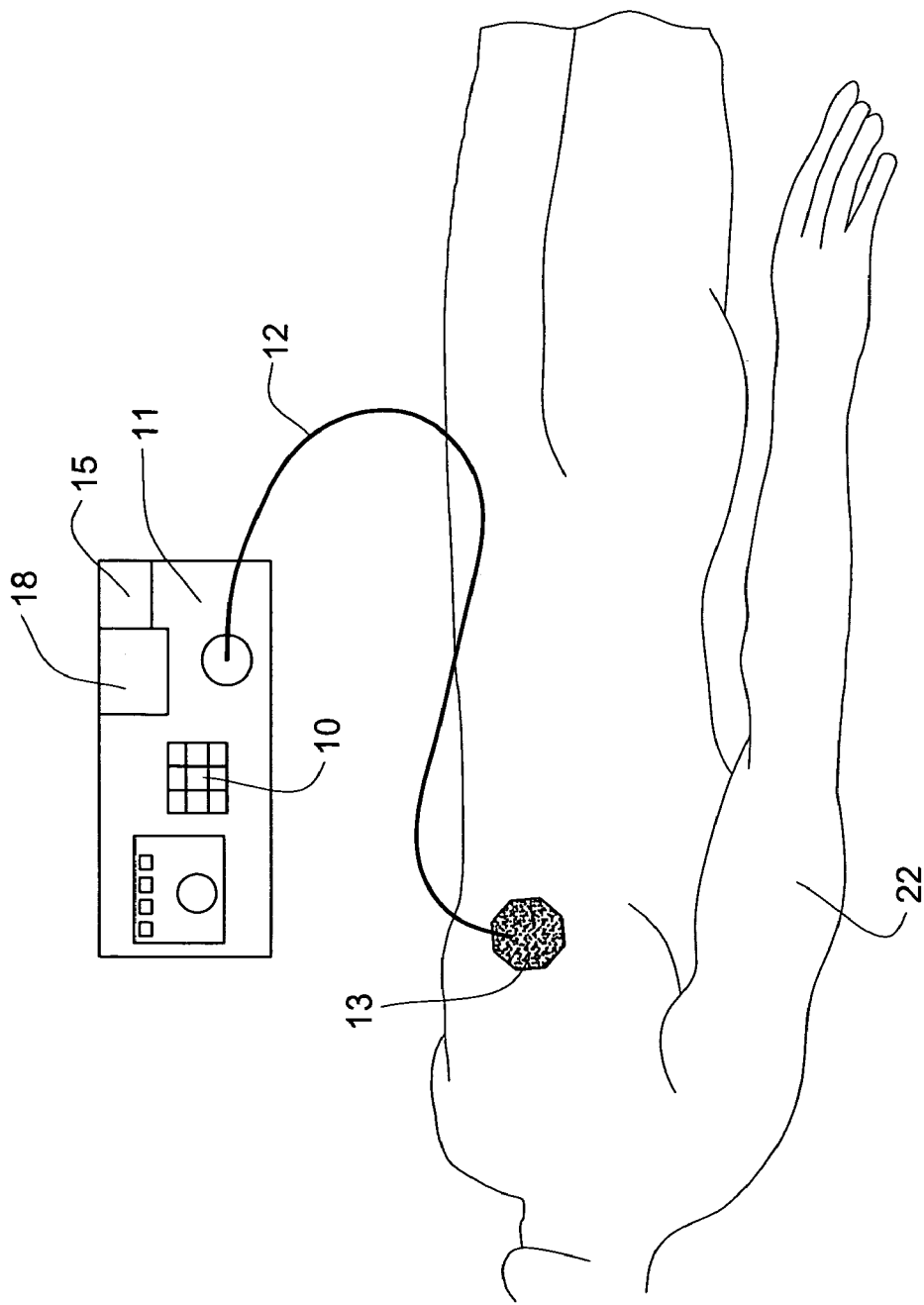
FIG. 1 shows a system for skin treatment in accordance with the invention.

FIG. 1 shows a system for irradiating skin in accordance with the invention. The system includes an applicator 13, to be described in detail below, configured to apply light energy to regions of skin of an individual 22. The applicator 13 is connected to a control unit 11 via a cable 12. The control unit 11 includes a power source 18 that is connected to one or more light sources in the applicator 13 via wires in the cable 12. The system also includes a source of negative pressure 15 such as a vacuum pump. As explained below, the vacuum pump is used to create a negative pressure in the applicator 13 by means of a vacuum hose in the cable 12 connecting the vacuum pump to the applicator 13. The control unit 11 has an input device such as a keypad 10 that allows an operator to input selected values of parameters of the treatment, such as the pulse duration and intensity of the light energy. The control unit 11 optionally contains a processor 9 for monitoring and controlling various functions of the device.

Figure 2:
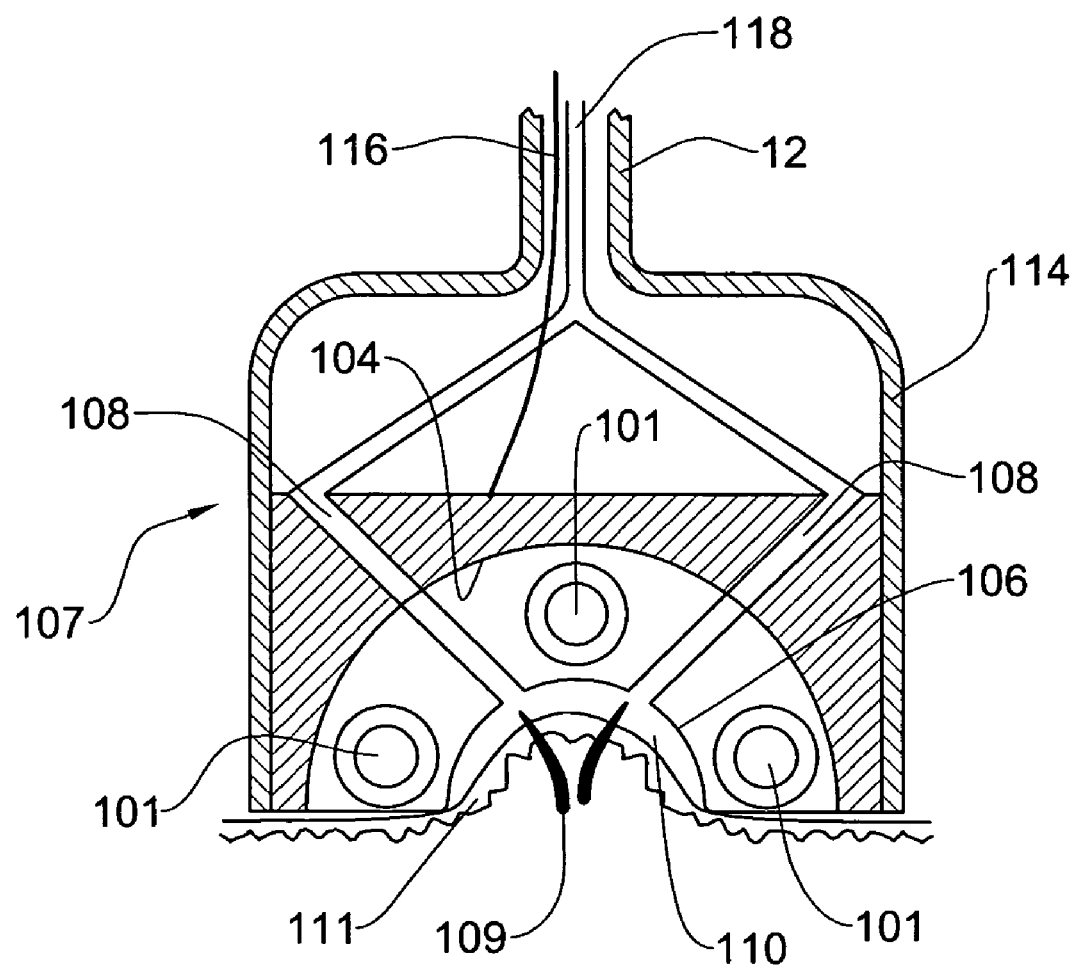
FIG. 2 shows an applicator for use in the system of FIG. 1 with multiple light sources distributed around the protruded skin.

FIG. 2 shows an applicator 107 that may be used for the applicator 13 in accordance with one embodiment of the invention. The applicator 13 has a housing 114 connected to the cable 12. The applicator 107 comprises lamps 101 surrounding a hollow cavity 110. Three lamps are shown in FIG. 2. This is by way of example only, and the applicator may have any number of lamps. The lamps are connected to the power source 18 by means of a wire 116 in the cable 12. The lamps 101 preferably generate broadband optical radiation. A reflector 104 reflects the optical radiation generated by the lamps 101 into the cavity 110 providing essentially uniform energy distribution over the cavity surface. An optical filter 106 transmits into the cavity the portion of the radiation that is safe for the skin and selectively absorbed by the target. The filter 106 alternatively may be in the form of a coating applied to the surface of the lamps 101. Vacuum suction through inlets 108 via a vacuum hose 118 in the cable 12 creates a negative pressure on the skin surface 111 causing the skin surface 111 to protrude into the cavity 110. Thus, the roots of the hairs 109 are irradiated from three sides. This heats a skin target inside the protruding region of skin, such as the root hairs 109, so as to damage the target.

The lamps 101 may be lasers, a filament lamp or LED (Light Emitting Diode). The number of light sources may be one or more. The light energy is preferably applied in a pulsed manner, in which case the light pulses are preferably synchronized with skin protrusion.

The invention can be used for the treatment of several different aesthetic procedures such as hair removal, vascular lesion treatment, pigmented lesion treatment, acne treatment, collagen remodeling.

The parameters for the skin treatment may be, for example as follows:
 Cavity size from 2 mm to 10 mm;
 Wavelength range of 500 to 1200 nm.
 Light pulse duration of 1 ms to 1000 ms
 Energy density on the skin surface from 2 to 30 J/cm$^2$.

The invention claimed is:

1. A system for the treatment of a skin comprising an applicator having a cavity disposed in the applicator so as to receive the skin therein when the applicator in use, the applicator comprising one or more light sources configured to irradiate the cavity with broadband optical energy simultaneously from at least two directions, a curved light reflector located within the cavity for reflecting light from the one or more light sources to the cavity, and a protruding mechanism configured to cause a region of skin to protrude above surrounding skin into the cavity when the applicator is applied to the skin.

2. The system according to claim 1, wherein the system further comprises a controller for generating light pulses by the one or more light sources.

3. The system according to claim 1, wherein optical energy produced by the one or more light sources has wave lengths in the range of 500 nm to 1200 nm.

4. The system according to claim 1, wherein the protruding mechanism involves generating a negative pressure in the cavity.

5. A method for treating skin with optical energy comprising:
  (a) applying to the skin an applicator having a cavity disposed in the applicator so as to receive the skin therein when the applicator is in use, the applicator comprising one or more broadband light sources and a curved light reflector located within the cavity for reflecting light from the one or more broadband light sources to irradiate protruding skin simultaneously from at least two directions when the applicator is applied to the skin;
  (b) causing a region of skin to protrude into the cavity; and
  (c) irradiating the protruding region of skin with optical energy from the one or more light sources simultaneously from at least two directions.

6. The method according to claim 5, wherein the optical energy is applied in pulses.

7. The method according to claim 5, wherein the optical energy has wavelengths in the range of 500 nm to 1200 nm.

* * * * *